United States Patent
Nagao et al.

(10) Patent No.: US 6,835,852 B2
(45) Date of Patent: Dec. 28, 2004

(54) PROCESS FOR PRODUCING TRIMELLITIC ACID

(75) Inventors: Shinichi Nagao, Kurashiki (JP); Ikutaro Kuzuhara, Kurashiki (JP); Hiroshi Ogawa, Kurashiki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/657,155

(22) Filed: Sep. 9, 2003

(65) Prior Publication Data
US 2004/0054219 A1 Mar. 18, 2004

(30) Foreign Application Priority Data
Sep. 11, 2002 (JP) ........................................ 2002-265655

(51) Int. Cl.⁷ ............................................. C07C 51/16
(52) U.S. Cl. ...................................................... 562/413
(58) Field of Search ........................................ 562/413

(56) References Cited

U.S. PATENT DOCUMENTS 3,491,144 A    1/1970   Ember et al.

FOREIGN PATENT DOCUMENTS

| | | |
|---|---|---|
| EP | 1 167 335 A | 1/2002 |
| GB | 907 926 A | 10/1962 |
| JP | 58-2222 | 1/1983 |
| WO | WO 98 55441 A | 12/1998 |

Primary Examiner—Paul J. Killos
(74) Attorney, Agent, or Firm—Sughrue Mion, PLLC

(57) ABSTRACT

A process for producing trimellitic acid which comprises step A for oxidizing pseudocumene, thereby obtaining a reaction mixture comprising dimethyl benzoic acid, dimethyl benzyl alcohol, and dimethyl benzaldehyde, step B for separating dimethyl benzoic acid, dimethyl benzyl alcohol and dimethyl benzaldehyde from the reaction mixture obtained in step A, step C for oxidizing dimethyl benzyl alcohol separated in step B, thereby obtaining dimethyl benzoic acid and dimethyl benzyl aldehyde and then feeding dimethyl benzoic acid and dimethyl benzyl aldehyde thus obtained to step B, and step D for oxidizing dimethyl benzoic acid and/or dimethyl benzaldehyde separated in step B, thereby obtaining trimellitic acid.

15 Claims, No Drawings

PROCESS FOR PRODUCING TRIMELLITIC ACID

BACKGROUND OF THE INVENTION

1) Field of the Invention

The present invention relates to a process for producing trimellitic acid by liquid phase oxidation of pseudocumene as a starting material, and specifically to a process for producing trimellitic acid which comprises oxidizing pseudocumene as a starting material in water solvent and producing intermediate products step by step and oxidizing thereof, thereby producing trimellitic acid of a final product in a high yield.

2) Prior Art

Terephthalic acid has been industrially produced in many states by air oxidation of p-xylene in acetic acid solvent in the presence of a bromine-transition metal catalyst. In a liquid phase oxidation reaction employing aromatic hydrocarbons as raw material, it is indispensable to use acetic acid as a solvent in order to obtain aromatic polycarboxylic acids. When acetic acid is used as such solvent, loss of acetic acid occurs by combustion.

Pseudocumene is oxidized with air in the presence of a heavy metal catalyst in the same manner as other alkyl aromatic compounds, whereby trimellitic acid is produced. However, it is known that trimellitic acid thus produced forms a complex with a heavy metal(s) due to ortho structure of two carboxylic groups in trimellitic acid to cause deactivation of the catalyst, so that its yield is lower than that in other alkyl aromatic compounds.

As a conventional process for producing trimellitic acid, U.S. Pat. No. 3,491,144 discloses a process for producing trimellitic acid which comprises initially oxidizing pseudocumene in acetic acid in the presence of Co bromide and adding Co, Mn and bromide thereto and further oxidizing at 200° C. or above.

Further, Japanese Patent Publication No.58-2222 discloses a process for producing trimellitic acid by oxidizing a polyalkyl-substituted aromatic aldehyde or oxide derivative thereof in water solvent with molecular oxygen.

In the production of trimellitic acid by oxidation of pseudocumene in acetic acid, loss of acetic acid as the solvent occurs by combustion. Further, there are some problems that when oxidation is performed in acetic acid solvent, it is avoidable to apply a batch wise. Thus, a process for producing trimellitic acid in a high yield without using acetic acid has been required.

On the other hand, the case where a polyalkyl-substituted aromatic aldehyde or oxide derivative thereof as a starting material is oxidized in water solvent has the defect that the polyalkyl-substituted aromatic aldehyde or oxide derivative thereof is expensive.

SUMMARY OF THE INVENTION

An object of the present invention is to provide a process for producing industrially and continuously trimellitic acid in a high yield by liquid phase oxidation of cheap pseudocumene as a starting material without using acetic acid as a solvent.

As a result to extensive studies to solve the prior art problems, the inventors have found that trimellitic acid can be obtained continuously in a high yield by oxidizing pseudocumene as a starting material and producing intermediate products step by step and oxidizing thereof and have accomplished the present invention.

That is, the present invention provides a process for producing trimellitic acid which comprises:

step A for oxidizing pseudocumene, thereby obtaining a reaction mixture comprising dimethyl benzoic acid, dimethyl benzyl alcohol, and dimethyl benzaldehyde step B for separating dimethyl benzoic acid, dimethyl benzyl alcohol and dimethyl benzaldehyde from the reaction mixture obtained in step A, step C for oxidizing dimethyl benzyl alcohol separated in step B, thereby obtaining dimethyl benzoic acid and dimethyl benzyl aldehyde and then feeding dimethyl benzoic acid and dimethyl benzyl aldehyde thus obtained to step B, and step D for oxidizing dimethyl benzoic acid and/or dimethyl benzaldehyde separated in step B, thereby obtaining trimellitic acid.

DETAILED DESCRIPTION OF THE INVENTION

The present invention will be described in more detail below.

(Step A)

Pseudocumene of a starting material for oxidation to be used in the present invention is present in a $C_9$ distillate of catalytic reforming oils or thermal cracking oils. Commercial products thereof separated by distillation can be used. The starting material for oxidation may contain dimethyl benzaldehyde (3,4-dimethyl benzaldehyde, 2,4-dimethyl benzaldehyde and 2,5-dimethyl benzaldehyde) and dimethyl benzoic acid(3,4-dimethyl benzoic acid, 2,4-dimethyl benzoic acid and 2,5-dimethyl benzoic acid) which are intermediate products of pseudocumene.

In step A, pseudocumene is subjected to liquid phase oxidation with molecular oxygen, whereby a reaction mixture comprising dimethyl benzoic acid, dimethyl benzyl alcohol and dimethyl benzaldehyde is obtained. Herein, dimethyl benzoic acid, dimethyl benzyl alcohol and dimethyl benzaldehyde are general terms including 3,4-, 2,4- and 2,5 isomers (hereinafter, the same meaning so long as it is not sepecially mentioned).

In this reaction, it is preferable to use water as a solvent. In this case, the weight ratio (SR) of the solvent to pseudocumene is preferably in the range of 0.2 to 10 and more preferably in the range of 1 to 5. Further, it is preferable that dimethyl benzoic acid is used together with pseudocumene and present in the reaction system. In this case, it is preferable that an amount of dimethyl benzoic acid to the solvent is in the range of 0.1 to 40% by weight. Herein, new dimethyl benzoic acid may be fed or dimethyl benzoic acid separated in step B described later may be circulated and used. When dimethyl benzoic acid is used and present together with pseudocumene as a starting material in water as a solvent, the selectivity of dimethyl benzaldehyde and dimethyl benzoic acid as intended products in step A is remarkably improved.

In step A, it is preferable to use at least one species of heavy metal compound as a catalyst. Herein, as the heavy metal, cobalt, manganese, iron, zirconium and cerium are used, among which cobalt and/or manganese is (are) preferable. It is preferable that these metals can be used as compounds such as organic acid salts, halogenides. It is preferable to use acetic acid salts thereof. The amount of the catalyst is in the range of 0.01 to 2% by weight and preferably in the range of 0.05 to 1% by weight as metal atom to pseudocumene as the starting material for oxidation.

In step A, the reaction temperature of the liquid phase oxidation is in the range of 90 to 170° C. and preferably in the range of 120 to 150° C. The reaction pressure is in the range of 0.1 to 2.0 MPaG, preferably in the range of 0.2 to 1.2 MPaG and more preferably in the range of 0.4 to 0.8 MPaG.

Trimellitic acid can be produced by using the reaction mixture obtained in step A as a raw material and performing its liquid phase oxidation. However, when produced dimethyl benzyl alcohol and unreacted pseudocumene are present in the raw material, the yield of trimellitic acid becomes low. Therefore, in the present invention, it is preferable to produce trimellitc acid via the following steps B, C and D.

(Step B)

In step B, dimethyl benzoic acid, dimethyl benzaldehyde and dimethyl benzyl alcohol are separated from the reaction mixture obtained in step A. The reaction mixture contains mainly unreacted pseudocumene, dimethyl benzoic acid, dimethyl benzaldehyde, dimethyl benzyl alcohol, water and catalyst components. The process for separating dimethyl benzoic acid, dimethyl benzaldehyde and dimethyl benzyl alcohol is not limited. For example, the reaction mixture is separated into an oily phase containing mainly pseudocumene, dimethyl bezoic acid, dimethyl benzoaldehyde and dimethyl benzyl alcohol and an aqueous phase. Then, the oily phase thus separated is subjected to vacuum distillation, whereby each distillate comprising each of pseudocumene, dimethyl benzoic acid, dimethyl benzaldehyde and dimethyl benzyl alcohol as main component is obtained. Dimethyl benzoic acid and dimethyl benzldehyde thus separated are oxidized in the following step D to covert to trimellitic acid. Components other than the main component may be contained in the above-mentioned each distillate. However, it is preferable that pseudocumene or dimethyl benzyl alcohol is not contained in dimethyl benzoic acid or dimethyl benzaldehyde to be fed in step D. When they are contained, they sometimes exert bad influence on the reaction in step D.

On the other hand, dimethyl benzyl alcohol separated in step B is oxidized in the following step C and reaction products obtained by oxidation are fed to step D via step B and effectively converted to trimellitic acid. Thus, according to the process of the present invention, trimellitic acid can be produced in a high yield without suffering any influence of dimethyl benzyl alcohol, Further, pseudocumene separated in Step B can be reused as the starting material in step A or as a solvent in step C.

(Step C)

In step C, dimethyl benzyl alcohol is subjected to liquid phase oxidation with molecular oxygen, whereby a reaction mixture comprising dimethyl benzoic acid and dimethyl benzaldehyde is obtained. The solvent to be used in the oxidation of dimethyl benzyl alcohol is aromatic hydrocarbons and/or water, preferably pseudocumene and/or water and more preferably pseudocumene. The amount of the solvent is in the range of 1 to 12 and preferably 2 to 6 as a weight ratio (SR) of the solvent to the raw material for oxidation (dimethyl benzyl alcohol). It is preferable to use pseudocumene and/or water as the solvent since any extra separation step is not required in feeding of the reaction mixture obtained in step C to step B. It is preferable that pseudocumene is contained in the reaction system of step C since the selectivity of dimethyl benzaldehyde and dimethyl benzoic acid as intended products in step C is improved.

In step C, it is preferable to use at least one species of heavy metal compound as a catalyst. Herein, cobalt, manganese, copper, iron, zirconium and cerium are used as the heavy metal, among which cobalt, manganese and/or copper is (are) preferable. These metals are used as compounds such as organic acid salts and halogenides. It is preferable to use organic acid salts thereof such as acetic acid salts and naphthenic acid salts.

The amount of the catalyst is in the range of 0.01 to 1% by weight and preferably 0.02 to 0.5% by weight as metal atom to dimethyl benzyl alcohol as a raw material for oxidation.

In step C, the reaction temperature of liquid phase oxidation is in the range of 120 to 210° C. and preferably 150 to 180° C. The reaction pressure is in the range of 0.0 to 2.0 MPaG, preferably 0.1 to 1.6 MPaG and more preferably 0.2 to 0.8 MPaG.

The reaction mixture obtained in step C is fed to step B and dimethyl benzoic acid and dimethyl benzaldehyde produced in step C are separated. Dimethyl benzoic acid and dimethyl benzaldehyde separated in step B are fed to the following step D. Herein, the process for feeding the reaction mixture of step C to step B is not limited. For example, it may be mixed in the reaction mixture of step A or it may be fed directly to each apparatus of step B such as a two-phase separator without any mixing.

(Step D)

In step D, dimethyl benxoic acid and/or dimethyl benzoaldehyde is subjected to liquid phase oxidation with molecular oxygen, whereby trimellitic acid is obtained. It is the most preferable that the solvent to be used is water. Also other solvents such as aliphatic carboxylic acid and a mixture of aliphatic carboxylic acid and water may be used. The weight ratio of the solvent to a raw material for oxidation is in the range of 0.2/1 to 10/1 and preferably 1/1 to 5/1.

In step D, it is preferable to use at least one species of heavy metal compound as a catalyst. Herein, cobalt, manganese, iron, zirconium and cerium are used as the heavy metal, among which cobalt and/or manganese is (are) preferable. These metals are used as compounds such as organic acid salts thereof and halogenides. It is preferable to use acetic acid salts thereof or bromide thereof.

Further, it is more preferable to use a bromine compound (s) as the catalyst. Examples of the bromine compound include inorganic bromides such as hydrogen bromide, sodium bromide and cobalt bromide and organic bromides such as tetrabromoethane, among which hydrogen bromide, cobalt bromide and manganese bromide are the most preferable.

The amount of the catalyst is in the range of 0.01 to 1% by weight and preferably 0.05 to 0.8 by weight as metal atom to the solvent. Total bromine concentration in the reaction system is in the range of 0.1 to 4.0% by weight and preferably 0.5 to 2.5% by weight as bromine atom to the solvent.

In step D, the reaction temperature of liquid phase oxidation is in the range of 160 to 260° C. and preferably 180 to 240° C. The reaction pressure is in the range of 0.5 to 5.0 MPaG and preferably 1.0 to 3.5 MPaG.

In each oxidation reaction of steps A, C and D, an oxygen-containing gas is used. Examples of the oxygen-containing gas include air, oxygen gas, mixed gases of oxygen and inert gases such as nitrogen and argon. Air is industrially the most advantageous.

A stirring vessel or a bubble column can be used as the oxidation reactor, among which a stirring vessel is preferable since stirring is sufficiently performed in the reactor. As the reaction process, all of batch wise, a semicontinuous process and a continuous process may be applied, among which a continuous process is preferable.

The oxygen concentration in an exhaust gas from the reactor is in the range of 0.1 to 8% by volume and preferably 1 to 5% by volume. It is preferable that the reactor is equipped with a reflux condenser to condense a large amount of solvent to be entrained in an exhaust gas and water to be produced in the oxidation reaction. Although the condensed solvent and water are usually refluxed to the reactor, a portion thereof is withdrawn also outside the reaction system in order to adjust a water concentration in the reactor.

PREFERRED EMBODIMENT OF THE INVENTION

The present invention will be described in more detail below, referring to Examples, which are not intended to limit the scope of the present invention.

EXAMPLE 1

(Step A)

A titanium autoclave of 2 L, equipped with a gas exhaust pipe with a reflux cooling tube, a gas injection nozzle and a stirrer was used as a reactor. Pseudocumene as a starting material at the rate of 331 g/h, 2,4-dimethyl benzoic acid at the rate of 55 g/h and water as a solvent at the rate of 342 g/h were fed to the reactor. Cobalt acetate tetrahydrate salt as a catalyst was added thereto so as to maintain a cobalt concentration of 500 ppm to the solvent. The reactor interior temperature was raised in a nitrogen atmosphere. Air was introduced therein at 120° C. under 0.4 MPaG and the continuous reaction was performed in a residence time of 50 minutes.

(Step B)

The reaction mixture obtained in the above-mentioned reaction was standing to separate into an aqueous phase and an oily phase comprising pseudocumene. This oily phase was subjected to vacuum distillation under 200 torr in a distillation column corresponding to the theoretical step of 8 steps thereby separating pseudocumene. Then, the oily phase separated pseudocumene is subjected to vacuum distillation under 20 torr in a distillation column corresponding to the theoretical step of 15 steps, whereby each distillate comprising each of dimethyl benzoic acid, dimethyl benzaldehyde and dimethyl benzyl alcohol as a main component was separated.

(Step C)

Dimethyl benzyl alcohol separated as a raw material at the rate of 200 g/h and pseudocumene as a solvent at the rate of 800 g/h were fed to the same reactor as described above. Manganese naphthenate and copper naphthenate as a catalyst were added thereto so as to maintain manganese concentration 200 ppm and copper concentration 50 ppm to the solvent. The reactor interior temperature was raised in a nitrogen atmosphere. Air was introduced therein at 170° C. under 0.4 MPaG and the continuous reaction was performed in a residence time of 120 minute.

The reaction mixture obtained in this reaction was added to the oily phase comprising pseudocumene in the above-mentioned step B.

(Step D)

Dimethyl benzoic acid at the rate of 50 g/h and dimethyl benzaldehyde at the rate of 10 g/h separated in the above-mentioned step B as a raw material and water as a solvent at the rate of 230 g/h were fed to a zirconium autoclave of 2 L, equipped with a gas exhaust pipe with a reflux condenser tube, a gas injection nozzle and a stirrer as a reactor. Manganese bromide tetrahydrate salt and hydrogen bromide as a catalyst were added thereto so as to maintain manganese concentration 0.43% by weight and bromine concentration 2.4% by weight. The reactor interior temperature was raised in a nitrogen atmosphere. Air was introduced therein at 220° C. under 3.3 MPaG and the continuous reaction was performed in a residence time of 90 minutes.

The reaction mixture thus obtained was analyzed. The yield of trimellitic acid to reacted pseudocumene was 71.0 mol %. The result is shown in Table 1.

EXAMPLE 2

The experiment was performed in the same manner as in Example 1 except that the feeding rate of dimethyl benzoic acid in step A was changed to 165 g/h. The result is shown in Table 1.

EXAMPLE 3

The experiment was performed in the same manner as in Example 1 except that cobalt naphthenate was used instead of manganese naphthenate in step C. The result is shown in Table 1.

Comparative Example 1

The experiment was performed in the same manner as in Example 1 except that the feeding rate of dimethyl benzoic acid in step A was changed to 0 g/h. The result is shown in Table 1.

Comparative Example 2

The experiment was performed in the same manner as in Example 1 except that the feeding rate of water as a solvent in step A was changed to 0 g/h. The result is shown in Table 1.

Comparative Example 3

The experiment was performed in the same manner as in Example 1 except that the feeding rate of pseudocumene as a solvent in step C was changed to 0 g/h. The result is shown in Table 1.

Comparative Example 4

A catalyst liquid mixed zirconium acetate, manganese acetate tetrahydrate salt, a 47% by weight hydrogen bromide aqueous solution, glacial acetic acid and water (zirconium concentration 0.01% by weight, manganese concentration 0.37% by weight, bromine concentration 0.4% by weight and water concentration 40% by weight) at the rate of 300 g/h and pseudocumene at the rate of 73 g/h were fed to a zirconium autoclave of 2 L, equipped with a gas exhaust pipe with a reflux condenser tube, a gas injection nozzle and a stirrer as a reactor. Air was introduced therein at 220° C. under 3.3 MPaG and oxidation was performed in a continuous one stage in a residence time of 90 minutes. The result is shown in Table 1.

As clear from Examples, intended trimellitic acid can be obtained in a high yield by oxidizing step by step pseudocumene as a starting material in a liquid phase according to the process of the present invention. The process of the present invention has a very large industrial significance since liquid phase oxidation of cheap pseudocumene is continuously performed.

TABLE 1

|  | Example 1 | Example 2 | Example 3 | Comp. Ex. 1 | Comp. Ex. 2 | Comp. Ex. 3 | Comp. Ex. 4 |
| --- | --- | --- | --- | --- | --- | --- | --- |
| Step A |  |  |  |  |  |  |  |
| PCM (mol %) | 12.5 | 12.1 | 12.5 | 13.2 | 98.5 | 12.5 | — |
| DMBA (mol %) | 1.5 | 4.8 | 1.5 | 0.0 | 1.5 | 1.5 | — |
| Water (mol %) | 86.0 | 83.1 | 86.0 | 86.8 | 0.0 | 86.0 | — |
| Acetic acid (mol %) | 0.0 | 0.0 | 0.0 | 0.0 | 0.0 | 0.0 | — |
| Catalyst species | Co | Co | Co | Co | Co | Co | — |
| Step C |  |  |  |  |  |  |  |
| DMBALc (mol %) | 16.7 | 16.7 | 16.7 | 16.7 | 16.7 | 100.0 | — |
| PCM (mol %) | 83.3 | 83.3 | 83.3 | 83.3 | 83.3 | 0.0 | — |
| Catalyst species | Mn + Cu | Mn + Cu | Co + Cu | Mn + Cu | Mn + Cu | Mn + Cu | — |
| Step D |  |  |  |  |  |  |  |
| DMBA + DBAL (mol %) | 3.2 | 3.2 | 3.2 | 3.2 | 3.2 | 3.2 | — |
| Water (mol %) | 96.8 | 96.8 | 96.8 | 96.8 | 96.8 | 96.8 | — |
| TMA yield (mol %) (based on reacted PCM) | 71.0 | 69.7 | 66.6 | 56.9 | 63.6 | 48.6 | 50.2 |

PCM: pseudocumene
DMBA: dimethyl bezoic acid
DBAL: dimethyl benzaldehyde
DMBALc: dimethyl benzyl alcohol
TMA: trimellitic acid

What is claimed is:

1. A process for producing trimellitic acid which comprises:
   step A for oxidizing pseudocumene, thereby obtaining a reaction mixture comprising dimethyl benzoic acid, dimethyl benzyl alcohol, and dimethyl benzaldehyde
   step B for separating dimethyl benzoic acid, dimethyl benzaldehyde and dimethyl benzyl alcohol from the reaction mixture obtained in step A,
   step C for oxidizing dimethyl benzyl alcohol separated in step B, thereby obtaining dimethyl benzoic acid and dimethyl benzyl aldehyde and then feeding dimethyl benzoic acid and dimethyl benzyl aldehyde thus obtained to step B, and
   step D for oxidizing dimethyl benzoic acid and/or dimethyl benzaldehyde separated in step B thereby obtaining trimellitic acid.

2. The process according to claim 1, wherein water is used as a solvent and dimethyl benzoic acid is used and present together with pseudocumene in the oxidation reaction of step A.

3. The process according to claim 2, wherein the weight ratio of the solvent to pseudocumene is in the range of 0.2 to 10.

4. The process according to claim 2, wherein the amount of dimethyl benzoic acid in relation to the solvent is in the range of 0.1 to 40% by weight.

5. The process according to anyone of claim 1, 2, 3, or 4 wherein at least one species of heavy metal compound is used as a catalyst and the reaction temperature is in the range of 90 to 170° C. and the reaction pressure is in the range of 0.1 to 2.0 MPaG in step A.

6. The process according to claim 5, wherein said heavy metal is cobalt and/or manganese and the amount of the catalyst is in the range of 0.01 to 2 by weight as metal atom to pseudocumene.

7. The process according to claim 1, wherein at least one species of heavy metal compound is used as a catalyst and aromatic hydrocarbons are used as a solvent and the reaction temperature is in the range of 120 to 210° C. and the reaction pressure is in the range of 0.1 to 2.0 MPaG in step C.

8. The process according to claim 7, wherein said heavy metal is at least one metal selected from the group consisting of cobalt, manganese and copper and the amount of the catalyst is in the range of 0.01 to 1% by weight as metal atom to dimethyl benzyl alcohol.

9. The process according to claim 7, wherein the weight ratio of the solvent to dimethyl benzyl alcohol is in the range of 1 to 12.

10. The process according to claim 1 wherein at least one species of heavy metal compound and a bromine compound are used as a catalyst and water and/or aliphatic carboxylic acid is (are) used as a solvent in step D.

11. The process according to claim 10, wherein said heavy metal is cobalt and/or manganese and the total amount of heavy metal is in the range of 0.01 to 1% by weight as metal atom to solvent.

12. The process according to claim 10 or 11, wherein the total bromine concentration in the reaction system is in the range of 0.1 to 4.0% by weight as bromine atom to the solvent.

13. The process according to claim 1, wherein step A, step C and step D are conducted in a continuous process.

14. The process according to claim 3, wherein the amount of dimethyl benzoic acid in relation to the solvent is in the range of 0.1 to 40% by weight.

15. The process according to claim 14 wherein at least one species of heavy metal compound is used as a catalyst and the reaction temperature is in the range of 90 to 170° C. and the reaction pressure is in the range of 0.1 to 2.0 MpaG in step A.

* * * * *